United States Patent
DeYoung et al.

(10) Patent No.: US 6,878,346 B2
(45) Date of Patent: Apr. 12, 2005

(54) SERUM TRANSFER CUP (75) Inventors: Thomas DeYoung, Hopewell Junction, NY (US); John Voulgaris, Dobbs Ferry, NY (US); Loretta Vincent, Fishkill, NY (US)

(73) Assignee: Bayer Corporation, Tarrytown, NY (US)

( * ) Notice: Subject to any disclaimer, the term of this patent is extended or adjusted under 35 U.S.C. 154(b) by 3 days.

(21) Appl. No.: 10/430,226

(22) Filed: May 6, 2003

(65) Prior Publication Data

US 2003/0213312 A1 Nov. 20, 2003

Related U.S. Application Data (60) Provisional application No. 60/381,643, filed on May 17, 2002.

(51) Int. Cl.[7] .............................. B01L 3/00; G01N 1/00
(52) U.S. Cl. ............................ 422/102; 422/99; 73/864; 73/864.51; 73/864.59
(58) Field of Search .................... 422/99, 102, 104, 422/939, 940, 941; 73/864, 864.51, 864.59

(56) References Cited

U.S. PATENT DOCUMENTS

| | | |
|---|---|---|
| 3,680,967 A | 8/1972 | Engelhardt |
| 3,780,935 A | 12/1973 | Lukacs et al. |
| 3,807,955 A | 4/1974 | Note, Jr. et al. |
| 3,969,250 A | 7/1976 | Farr |
| 4,074,976 A | 2/1978 | Gower et al. |
| 4,463,616 A | 8/1984 | Blecher |
| 5,270,219 A | 12/1993 | DeCastro et al. |
| 5,277,873 A | 1/1994 | Hsei |
| 5,279,159 A | 1/1994 | Amelung |
| 5,424,837 A | 6/1995 | Porte et al. |
| 5,536,471 A | 7/1996 | Clark et al. |
| 5,556,599 A * | 9/1996 | Ahmed ...................... 422/102 |
| 5,739,441 A | 4/1998 | Friese et al. |
| 5,846,745 A | 12/1998 | Christensen et al. |
| 5,915,583 A * | 6/1999 | Cloonan et al. ......... 220/23.86 |
| 6,063,340 A | 5/2000 | Lewis et al. |
| 6,117,391 A | 9/2000 | Mootz et al. |
| 6,227,053 B1 * | 5/2001 | Purpura et al. ............... 73/627 |
| 6,598,474 B2 * | 7/2003 | Purpura et al. .......... 73/290 V |
| 2002/0121139 A1 * | 9/2002 | Purpura et al. .......... 73/290 V |

* cited by examiner

*Primary Examiner*—Maureen M. Wallenhorst
(74) *Attorney, Agent, or Firm*—Andrew L. Klawitter; Rodman & Rodman (57) ABSTRACT

The serum transfer cup is nestable in two different size blood collection tubes such as a 13 mm diameter sample tube and a 16 mm diameter sample tube of the same axial length. The serum transfer cup includes a flange stepped down from a top edge of the cup by a distinctive axial distance that permits ultrasonic identification of the presence of the serum transfer cup regardless of which sample tube nests the serum transfer cup. The serum transfer cup has a higher elevation in the 13 mm sample tube than in the 16 mm sample tube, and the different flange heights can be detected using ultrasonic signals. Thus ultrasonic measurement of the flange position of the nested serum transfer cup identifies the presence of different serum transfer cups in the 13 mm sample tube and in the 16 mm sample tube, and also identifies the 13 mm and 16 mm sample tubes with the nested serum transfer cups.

12 Claims, 4 Drawing Sheets

SERUM TRANSFER CUP

BACKGROUND OF THE INVENTION

This invention is directed to a serum transfer cup for holding a relatively small amount of blood serum poured from a blood collection tube.

Blood collection tubes are made in a variety of different sizes, such as 13 mm diameter through 17 mm diameter, and in different lengths that range from 75 mm to over 100 mm. Two popular size blood collection tubes in general use are 13 mm and 16 mm diameter tubes having a length of 75 mm, such as manufactured by Becton-Dickenson.

When a lab draws whole blood from a patient it is usually collected in a standard blood collection tube. The standard blood collection tube with whole blood is generally spun in a centrifuge to separate red blood cells from serum. A gel separator that is provided in the blood collection tube maintains the serum separate from the red blood cells after the centrifuge operation. Thus when the blood collection tube with the whole blood is spun, the serum rises above the gel separator and the red blood cells remain below the gel separator.

The separated serum in the blood collection tube is the material that is used for performing test assays.

In an automated assay system an aspiration/dispensation probe is directed into the blood collection tube to aspirate serum. After several aspirations of serum are taken from the collection tube the serum level will recede and eventually come very close to the gel separator. If further serum aspiration is undertaken when the serum level is close to the gel separator there is a possibility that the aspiration probe may become clogged with gel.

In order to conserve serum when the serum level is in close proximity to the gel separator and not risk clogging of the aspiration probe a technician will usually pour serum from the blood collection tube into a smaller container. Although the volume of serum in the smaller container is essentially the same as it was in the blood collection tube, the column height of serum in the smaller container is increased because the smaller container has a smaller diameter than the blood collection tube. It should be noted that only the serum is poured from the blood collection tube to the smaller container or serum transfer cup.

The blood collection tube usually has a bar code label that identifies the patient from whom the blood was drawn. The serum transfer cup generally does not have a bar code label. Thus, after the serum is poured from a blood collection tube into the serum transfer cup the serum transfer cup is nested back in the open end of the blood collection tube to maintain integrity of patient identification with respect to serum in the serum transfer cup.

In summary, the blood collection tube which has whole blood is spun down to separate serum from red blood cells. The separated serum is usually aspirated down to a level where it is then poured into a serum transfer cup. The serum transfer cup is nested in the blood collection tube to permit continued use of the serum without losing patient identification. The serum transfer cup conserves the serum by rearranging it into a usable column of fluid that facilitates further aspiration of small amounts of serum by an aspiration probe. In many instances use of the serum transfer cup eliminates the need to redraw blood from a patient in order to obtain more serum.

A known serum transfer cup is sold under the trade designation Ezee-Nest®. However, in an automated assay system that uses robotics to move blood collection tubes around the assay system the Ezee-Nest® serum transfer cup may rattle or vibrate inside the blood collection tube, which can result in spillage of serum from the serum transfer cup. A serum spill may require redrawing of whole blood from a patient, and can also contaminate blood samples in the nearby blood collection tubes within the automatic assay system.

It is thus desirable to provide a serum transfer cup that can fit with minimal clearance in a blood collection tube to minimize or prevent rattling or vibration of the serum transfer cup while the blood collection tube is being transported in an automated assay system.

During automatic liquid level sensing there must be a predetermined minimum height of serum underneath the tip of the probe. If a probe goes below the minimum liquid level height there is a danger of mis-sensing the liquid level or mis-aspirating the serum, whereby an incomplete aspiration can occur in which some air is aspirated instead of a complete serum aspiration.

When an expected volume of serum that is critical for a test assay is not aspirated and some air is aspirated instead of serum, there will be an erroneous assay. Therefore it is desirable to have a predetermined minimum level of serum beneath the last viable serum aspiration so that the probe does not mis-aspirate serum or crash into the bottom of a serum container and cause damage to the probe.

It is also desirable to provide a serum transfer cup that makes maximum use of relatively small amounts of serum remaining in a blood collection tube, provides a safe clearance height up from the bottom of the inside of a serum transfer cup and allows an aspiration probe to have a safe clearance of at least a millimeter on either side of the probe to the closest wall of the serum transfer cup.

It is also desirable to have one serum transfer cup that can fit into two different size blood collection tubes, such as a 13 mm and a 16 mm collection tube, without troublesome rattling or vibration.

DESCRIPTION OF THE DRAWINGS

In the accompanying drawings.

DESCRIPTION OF THE INVENTION

Referring to the drawings, a serum transfer cup incorporating one embodiment of the invention is generally indicated by the reference number 10. The serum transfer cup 10 is a generally tubular member preferably formed of a transparent plastic material such as polystyrene. The serum transfer cup 10, which can be molded in one piece, includes an open end 12 bordered by an annular top edge 14 having a first outside diameter. The top edge 14 has an inside annular chamfer 16 preferably ½ mm×60 degrees.

Figure 1:
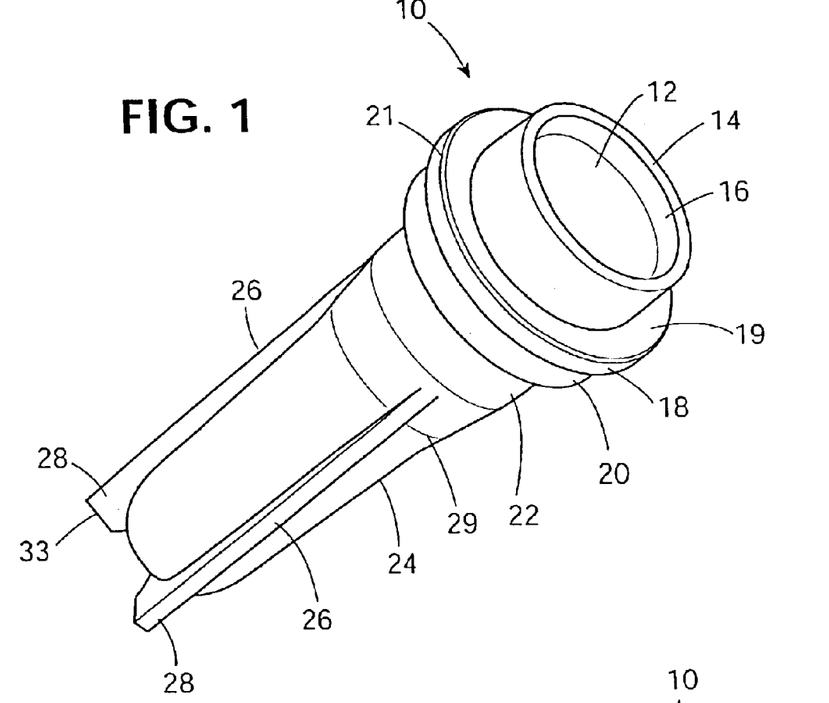
FIG. 1 is a perspective view of the serum transfer cup incorporating one embodiment of the invention.
Figure 2:
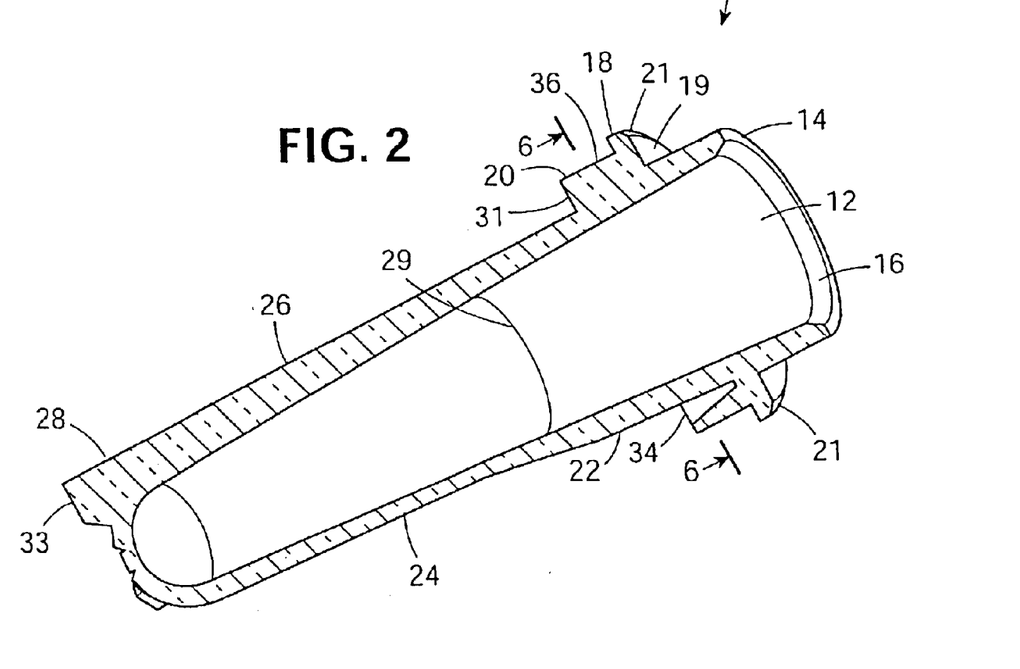
FIG. 2 is a sectional view thereof.
Figure 3A:
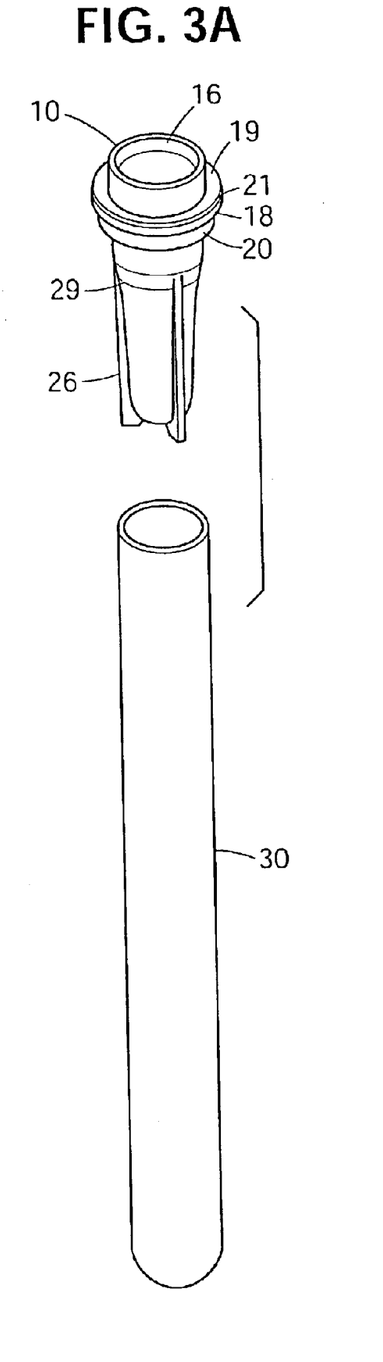
FIG. 3A is a an exploded perspective view of the serum transfer cup and a 13 mm sample tube prior to nesting of the serum transfer cup in a 13 mm blood collection tube.
Figure 3B:
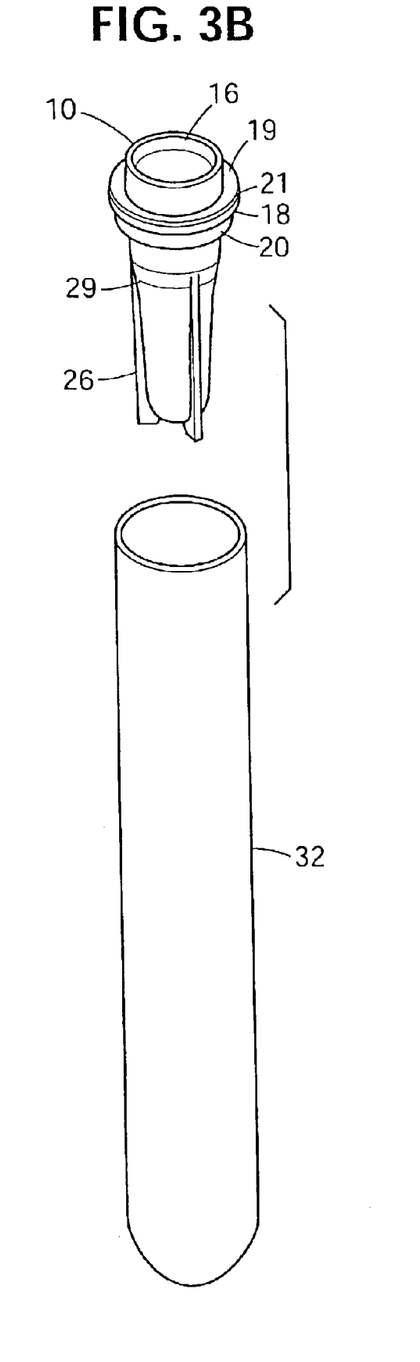
FIG. 3B is a view similar to FIG. 3A prior to nesting of the serum transfer cup in a 16 mm blood collection tube.
Figure 4A:
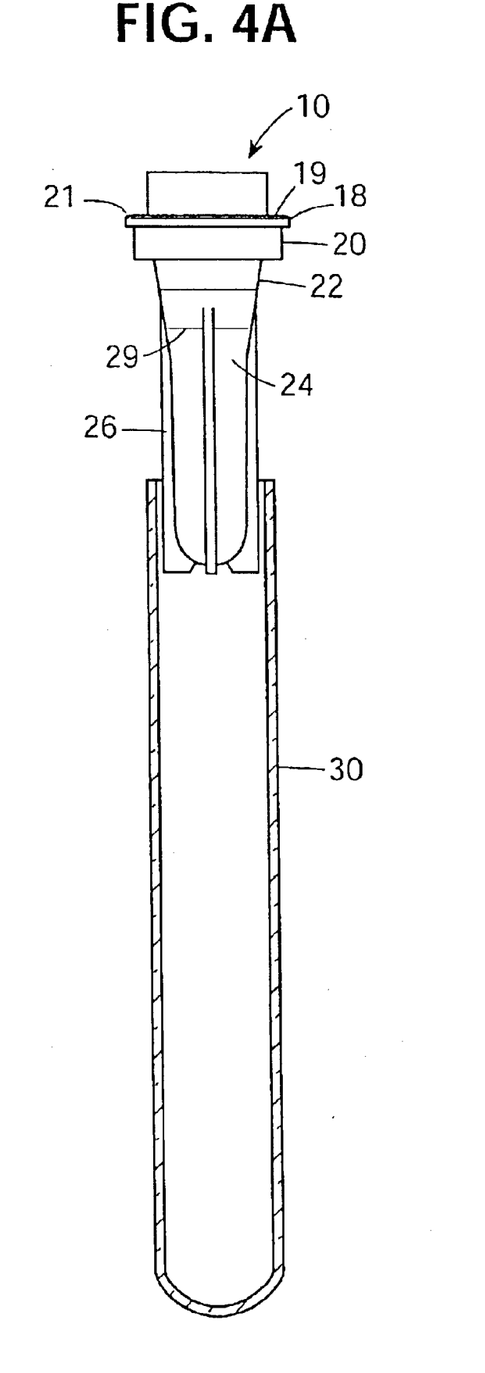
FIG. 4A is a view similar to FIG. 3A showing partial nesting of the serum transfer cup in the 13 mm blood collection tube, which is shown in section.
Figure 4B:
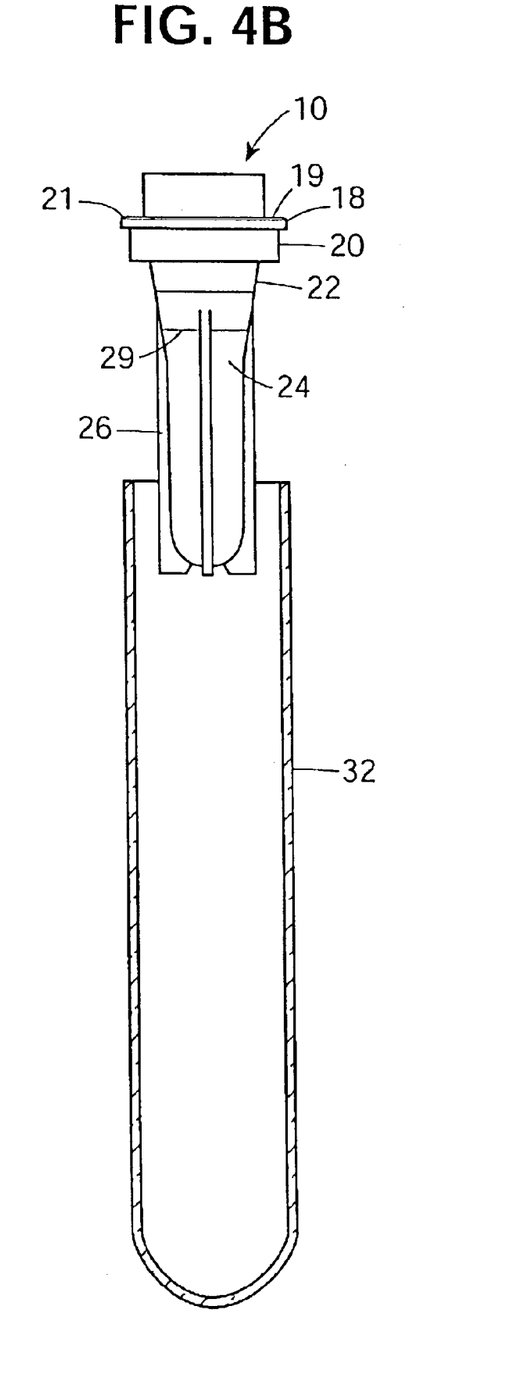
FIG. 4B is a view similar to FIG. 4A showing the serum transfer cup partially nested in the 16 mm blood collection tube, which is shown in section.

An annular support flange 18 on an enlarged neck or enlarged annular collar 20 has an outside diameter of greater magnitude than the diameter of the top edge 14 and the enlarged annular collar 20. The flange 18 thus projects radially beyond the enlarged annular collar 20. The annular support flange 18 includes a flange top surface 19 that is stepped down or spaced a first predetermined distance from the top edge 14. The top surface 19 has a peripheral edge chamfer 21 (FIGS. 1 and 2), preferably ½ mm×60 degrees.

Figure 6:
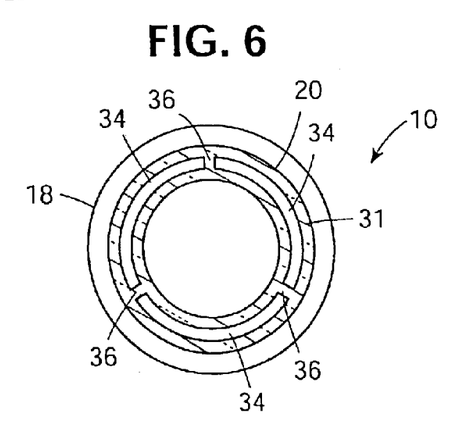

The enlarged annular collar 20, is an area of increased wall thickness of the serum transfer cup 10. A bottom surface 31 (FIGS. 2 and 6) of the annular collar 20 is thus provided with sectored recesses 34 separated by internal radial ribs 36. The recesses 34 help to eliminate the formation of shrinkage concavities that might occur at areas of increased thickness during molding of the serum transfer cup 10.

The serum transfer cup 10 also includes a reduced neck 22 below the enlarged annular collar 20 and a reduced diameter container section 24 with three vertical ribs 26. The reduced neck 22 and the reduced diameter container section 24 are together referred to as the tubular section below the annular collar 20. The ribs 26 on the container section 24 have footing portions 28 with flat ends 33 (FIGS. 1, 2, 5A and 5B) that extend below the closed end of the serum transfer cup 10. A volume measurement line 29 is provided on the outside surface of the container section 24 to facilitate determination of serum volume in the serum transfer cup 10.

Figure 5A:
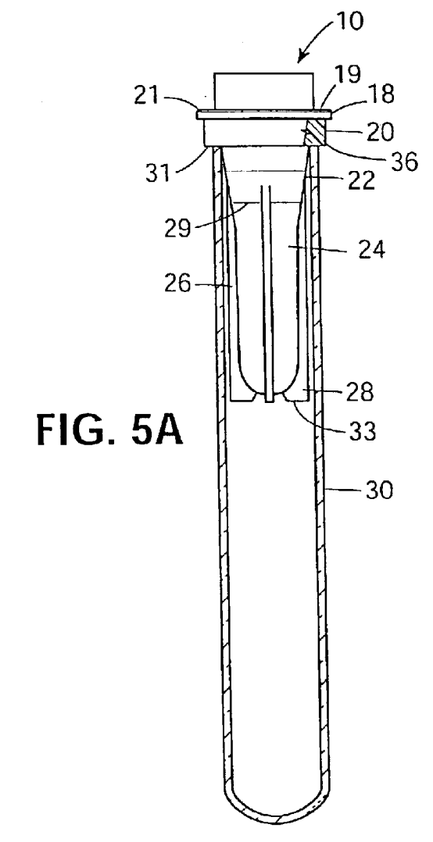
FIG. 5A is a view similar to FIG. 4A showing the serum transfer cup fully nested in the 13 mm blood collection tube.
Figure 5B:
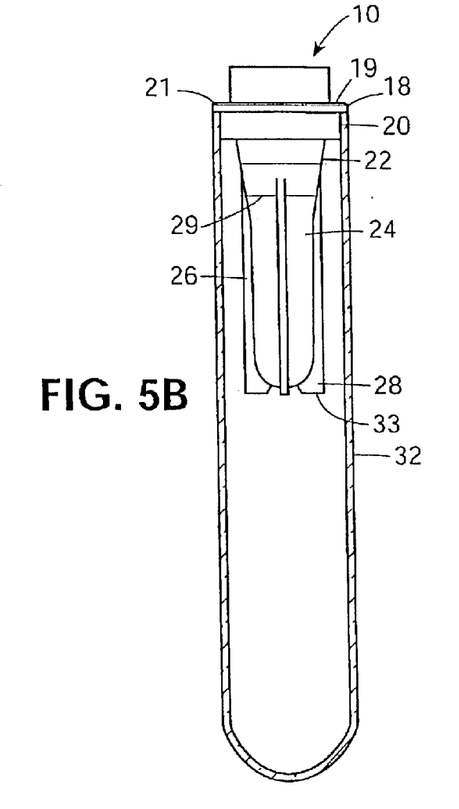
FIG. 5B is a view similar to FIG. 4A showing the serum transfer cup fully nested in the 16 mm blood collection tube; and, FIG. 6 is a sectional view taken on the line 6—6 of FIG. 2.

The serum transfer cup 10 is sized such that it can be seated or nested on the open end of a standard 13 mm blood collection tube 30 or 16 mm blood collection tube 32 (FIGS. 5A and 5B). Both the 13 mm and 16 mm blood collection tubes 30 and 32 are of substantially the same height, such as 75 mm. Blood collection tubes 30 and 32 are also referred to as sample tubes, since they are often used to collect and contain blood samples. Therefore the blood collection tubes 30 and 32 will hereafter be referred to as sample tubes.

When the serum transfer cup 10 is nested on the 13 mm sample tube 30 (FIG. 5A) the radial ribs 36 of the collar bottom surface 31 rest on the open end of the sample tube 30 (FIG. 5A). The collar bottom surface 31 thus constitutes a seating surface or support surface for the serum transfer cup 10 when the transfer cup 10 is nested on the 13 mm sample tube 30. Under this arrangement the flange top surface 19 is spaced above the open end of the sample tube 30 by an amount equal to the axial height of the enlarged neck 20, from the engagement surface 31 to the annular flange 18, plus the axial thickness of the annular flange 18.

When the serum transfer cup 10 is nested on the 16 mm sample tube 32 the annular support flange 18 rests directly upon the open end of the sample tube 32 (FIG. 5B), and the enlarged collar portion 20 and the tubular sections 22, 24 are recessed in the open end of the sample tube 32. The outside diameter of the collar portion 20 is of lesser magnitude than the inside diameter of the sample tube 32 to permit easy nesting and removal of the serum transfer cup 10 from the sample tube 32.

The outside diameter of the annular flange 18 is of greater magnitude than the outside diameter of the 13 mm sample tube and at least the same diameter as the outside diameter of the 16 mm sample tube.

The elevation of the flange top surface 19 in the 13 mm sample tube 30 (FIG. 5A) is higher than the elevation of the flange top surface 19 in the 16 mm sample tube 32 (FIG. 5B), as will be apparent from a side-by-side comparison of FIGS. 5A and 5B. This height difference of flange top surface 19 for the 13 mm and 16 mm sample tubes also exists when a plurality of 13 mm and 16 mm sample tubes 30 and 32, with nested serum transfer cups 10, are supported in a sample tube rack (not shown).

The elevation of the flange top surface 19 is detectable by ultrasonic waves when different serum transfer cups 10 are respectively seated in 13 mm sample tubes 30 and 16 mm sample tubes 32 that are collectively supported in a sample tube rack (not shown). Therefore by ultrasonically measuring the distance between a fixed overhead ultrasonic transmitter (not shown) and height of the flange top surface 19, when a serum transfer cup 10 is nested in the 13 mm and 16 mm sample tubes, one can determine the presence of the serum transfer cup 10 in the 13 mm sample tube 30 and in the 16 mm sample tube 32. Such ultrasonic measurement is usually carried out when different 13 mm and 16 mm sample tubes are supported in a sample tube rack that is caused to move in a predetermined travel path below the ultrasonic transmitter.

Thus an ultrasonic distance measurement of the flange top surface 19 of a nested serum transfer cup 10 can be used to identify whether a 13 mm sample tube 30 or 16 mm sample tube 32 is present. The flange 18 thus permits specific identification of the size of the sample tube 30 or 32 in which the serum transfer cup 10 is nested.

The step down of the flange 18 from the top edge 14 of the serum transfer cup 10 to the flange top surface 19 provides the serum transfer cup 10 with a unique dimensional profile that distinctively identifies the serum transfer cup. The step down distance of the flange 18 from the top edge 14 of the serum transfer cup 10 is distinctively unique to the serum transfer cup 10 and provides an ultrasonic measurement surface that, because of the unique distance of the flange 18 from the top edge 14, identifies the presence of the serum transfer cup 10 regardless of which sample tube 30 or 32 the serum transfer cup 10 is nested in.

It is necessary to distinguish between a 13 mm sample tube 30 and a 16 mm sample tube 32 in an automatic sampling system that employs robotics because a robot must know what type of sample tube 30 or 32 is being picked up.

Because the serum transfer cup 10 sits higher in the 13 mm sample tube 30 than in the 16 mm sample tube 32 the difference in the height of the flange 18, depending upon which sample tube 30 or 32 the serum transfer cup 10 is nested in, is determined during ultrasonic liquid level sensing. Therefore ultrasonic sensing can determine whether the serum transfer cup 10 is nested in a 13 mm sample tube 30 or a 16 mm sample tube 32.

During ultrasonic detection the ultrasonic transmitter (not shown) can only "see" down onto the top of the serum transfer cup 10 because the flange 18 of the serum transfer cup 10 covers the open end of both the 13 mm sample tube 30 and the 16 mm sample tube 32.

However, since a reflected ultrasonic signal corresponds to a specific distance of the reflection surface from the ultrasonic transmitter (not shown) it can be determined whether the serum transfer cup 10 is in a 13 mm sample tube 30 or a 16 mm sample tube 32. Therefore, an ultrasonic signal bounced or reflected from the flange 18 of a serum transfer cup 10 nesting in a 13×75 mm sample tube 30 is distinguishable from an ultrasonic signal bounced or reflected from the flange 18 of a serum transfer cup nesting in a 16×75 mm sample tube 32, because of the different height levels of the flange 18 on the nested serum transfer cup 10. Thus ultrasonic identification of a 13 mm sample tube 30 or 16 mm sample tube 32 is accomplished using the serum transfer cup 10.

The flange 18 of the serum transfer cup 10 thus provides a distinctively unique ultrasonic signature that identifies the presence of the serum transfer cup 10 and the type of sample tube 30 or 32 in which the serum transfer cup 10 is disposed. The peripheral edge chamfer 21 of the annular top flange 18 enables an ultrasonic signal to distinguish between annular support flanges 18 of adjacent serum transfer cups 10 that are supported at the same level and are located side by side in a rack.

The vertical ribs 26 on the serum transfer cup 10 minimize clearance between the transfer cup 10 and the inside surface of the 13 mm sample tube 30 and help prevent excessive rocking, rattling or vibration of the serum transfer cup 10 when it is in a 13 mm sample tube 30. The ribs 26 and the enlarged neck 20 also help reduce clearance of the serum transfer cup 10 from the inside surface of the 16 mm sample tube 32 and help prevent rocking, rattling or vibration of the serum transfer cup 10 when it is in a 16 mm sample tube 32. The flat ends 33 of the rib footing portions 28 that extend below the closed end of the serum transfer cup 10 permit the serum transfer cup 10 to stand upright on a flat surface.

As previously noted the inside chamfer 16 (FIG. 2) at the open end 12 of the serum transfer cup 10 has an angle of approximately 60 degrees. The chamfer 16 is a geometric aid to stabilize the lip of a sample tube 30 or 32 when serum from the sample tube is poured into the serum transfer cup 10. The chamfer 16 also ensures that the sample tube 30 or 32 does not slide off the open end 12 of the serum transfer cup 10 and spill serum during pouring of serum from the sample tube 30 or 32 to the serum transfer cup 10. Thus the mouth or lip chamfer 16 on the serum transfer cup 10 acts as a centering device to hold the open end of the collection tube 30 or 32 during pouring of serum from the sample tube into the serum transfer cup 10.

However the chamfer angle selected must be compatible with ultrasonic detection. For example a 45 degree chamfer at the open end 12 of the serum transfer cup 10 would also facilitate pouring stability of whole blood from a sample tube 30 or 32 to the serum transfer cup 10. It has been found that a 45 degree chamfer angle tends to reflect or scatter ultrasonic waves from one side of the open end 12 to the other side and then back up to an overhead ultrasonic receiver. Ultrasonic wave scattering of this type will provide confusing signal readings at the ultrasonic receiver.

It has also been found that a 60 degree chamfer angle at the open end 12 of the serum transfer cup 10 eliminates ultrasonic signal scattering back to the ultrasonic receiver by directing the ultrasonic waves away from the ultrasonic receiver. Thus ultrasonic signals reaching a 60 degree chamfer at the open end 12 of the serum transfer cup 10 are not received back by an ultrasonic receiver and therefore do not provide confusing signal readings.

A known rack (not shown) for holding both 13 mm sample tubes 30 and 16 mm sample tubes 32 includes a vertical "V" groove (not shown) that engages the outside diameter of the sample tube and a spring (not shown) that biases the sample tube against the "V" groove. Therefore, if a 13 mm sample tube 30 is placed in the rack it will sit in a unique position wherein the center of the 13 mm sample tube 30 will be closer to the apex of the "V" than the center of a 16 mm tube 32 which will stand further away from the apex of the "V" groove.

Thus there is an offset of the center of the 13 mm sample tube 30 relative to the center of the 16 mm sample tube 32 when both sample tubes 30 and 32 are in the same type of rack. The offset is proportional to the tube diameter and is approximately 1.8 mm for the 13 mm and 16 mm sample tubes.

Once the offset measurement between 13 mm and 16 mm sample tubes is known an aspiration probe (not shown) can be positioned to enter the serum transfer cup or sample tube along the centerline of the sample tube. When an ultrasonic identification determines that a sample tube is a 13 mm tube or a 16 mm tube 32 the corresponding offset measurement is provided to the aspiration probe mechanism (not shown) to ensure that the probe descends into the serum transfer cup 10 with adequate clearance from the sidewall of the serum transfer cup, or from the sidewall of the sample tube 30 or 32.

In view of the above, it will be seen that the several objects of the invention are achieved and other advantageous results attained.

A various changes can be made in the above constructions and methods without departing from the scope of the invention, it is intended that all matter contained in the above description or shown in the accompanying drawings shall be interpreted as illustrative and not in a limiting sense.

What is claimed is:

1. A serum transfer cup that is optionally supportable on either of two blood collection tubes of the same axial height but of different inside diameter and different outside diameter, wherein a first blood collection tube has a first inside diameter, and a second blood collection tube has a second inside diameter of smaller magnitude that the first inside diameter, said serum transfer cup comprising, a) a hollow tubular member with an axis, an open end and a generally tubular wall concentric to said axis, an external annular support flange on the tubular wall below the open end, said annular support flange having a flange top surface and a predetermined flange thickness, an enlarged annular collar portion adjacent and below the annular support flange and having a collar diameter of smaller diametrical magnitude than the first inside diameter to permit recession of the enlarged annular collar portion in the first blood collection tube, and a tubular section below the enlarged annular collar portion that is of smaller outside diametrical magnitude than the first and second inside diameters of the first and second blood collection tubes to permit recession of the tubular section in the first and second blood collection tubes, b) the external annular support flange having an outside flange diameter of greater magnitude than the outside diameter of the second blood collection tube and at least the same diameter as the outside diameter of the first blood collection tube, to permit seating of said annular support flange on the first. blood collection tube, said flange top surface being at a first uniquely identifiable axial distance below the open end of the serum transfer cup to permit ultrasonic identification of the serum transfer cup based on ultrasonic measurement information that identifies the first distinctively identifiable axial distance, and to permit ultrasonic identification of a nested combination of a first blood collection tube and serum transfer cup wherein the annular support flange of the serum transfer cup is seated on the first blood collection tube with the enlarged annular collar portion and the tubular section recessed in the first blood collection tube, the ultrasonic identification of the nested combination of the first blood collection tube and the serum transfer cup being based on ultrasonic measurement information that identifies the first distinctively identifiable axial distance to identify the serum transfer cup, and ultrasonic measurement information of the distance of the flange top surface on the first blood collection tube from an ultrasonic signal transmitter, c) the enlarged annular collar portion having an outside collar diameter of larger diametrical magnitude than the second inside diameter of the second blood collection tube to permit seating of a collar bottom surface of said enlarged collar portion on the second blood collection tube, said enlarged collar portion extending a second uniquely identifiable axial distance below the flange top surface to the collar bottom surface to permit ultrasonic identification of a nested combination of a second blood collection tube and serum transfer cup wherein the collar bottom surface is seated on the second blood collection tube with the tubular section recessed in the second blood collection tube, the ultrasonic identification of the nested combination of the second blood collection tube and the serum transfer cup being based on ultrasonic measurement information that identifies the first distinctively identifiable axial distance to identify the serum transfer cup, and ultrasonic measurement information of the distance of the flange top surface on the second blood collection tube from the ultrasonic signal transmitter.

2. The serum transfer cup as claimed in claim 1 wherein the tubular section includes a plurality of vertical ribs of predetermined height projecting radially outward from the tubular section such that the outermost portions of said ribs at any height level define a fixed diametrical magnitude.

3. The serum transfer cup as claimed in claim 2 having a closed end opposite the open end and the ribs extend below the closed end of the serum transfer cup in the form of footing portions with flat ends that permit the serum transfer cup to stand upright on a flat surface on said flat ends.

4. The serum transfer cup as claimed in claim 1 wherein the open end has an inside annular chamfer of approximately 60 degrees with respect to the open end.

5. The serum transfer cup as claimed in claim 1 being formed of a transparent material and including a volume measurement line at a predetermined axial height of the tubular section to facilitate volume measurement of serum in the serum transfer cup.

6. The serum transfer cup as claimed in claim 5 wherein the volume measurement line is formed on an outside surface of the serum transfer cup.

7. The serum transfer cup as claimed in claim 1 wherein the annular support flange has a peripheral edge with a peripheral chamfer of approximately 60 degrees with respect to the flange top surface.

8. A method of determining whether a serum transfer cup is supported on either of two different diameter blood collection tubes of the same axial height, but of different inside diameter and different outside diameter, wherein a first blood collection tube has an open end and a first inside diameter and a second blood collection tube has an open end and a second inside diameter of smaller magnitude than the first inside diameter comprising, a) forming a generally tubular serum transfer cup with a tubular wall having an open end, b) forming an external annular support flange of predetermined thickness on the tubular wall of the serum transfer cup below the open end with an outside flange diameter that is of greater magnitude than the second blood collection tube and at least the same diameter as the outside diameter of the first blood collection tube, and with a flange top surface that is at a first distinctively identifiable axial distance from the open end of the serum transfer cup, c) forming an enlarged annular collar portion on the tubular wall of the serum transfer cup, adjacent and below the annular support flange, with an outside collar diameter that is of lesser magnitude than the first inside diameter of the first blood collection tube to permit recession of the annular collar portion inside the first blood collection tube, and of greater magnitude than the inside diameter of the second blood collection tube to permit seating of a collar bottom surface of the enlarged collar portion on the second blood collection tube, and providing the collar bottom surface at a second distinctively identifiable axial distance from the flange top surface, d) forming a tubular section of the serum transfer cup below the enlarged collar portion with less outside diametrical magnitude than the first and second inside diameter of the first and second blood collection tubes to permit recession of the tubular section in the first and second blood collection tubes, e) supporting one said serum transfer cup on the first blood collection tube such that the external annular support flange is seated upon the open end of the first blood collection tube and the enlarged annular collar portion and the tubular section of the one said serum transfer cup are recessed in the first blood collection tube, whereby the one said serum transfer cup and the first blood collection tube form a first nested combination, f) detecting the first nested combination of the first blood collection tube including the one said serum transfer cup by providing ultrasonic measurement information that identifies the first distinctively identifiable axial distance between the open end of the serum transfer cup and the flange top surface to identify the one said serum transfer cup while the one said serum transfer cup is supported on the first blood collection tube, and providing additional ultrasonic measurement information that identifies the distance of the flange top surface from an ultrasonic signal transmitter when the one said serum transfer cup is supported on the first blood collection tube, g) supporting another said serum transfer cup on the second blood collection tube such that the collar bottom surface is seated upon the open end of the second blood collection tube, while the flange top surface of the other said serum transfer cup is elevated above the open end of the second blood collection tube by an amount that corresponds to the second distinctively identifiable axial distance, and the tubular section of the other said serum transfer cup is recessed in the second blood collection tube, whereby the other said serum transfer cup and the second blood collection tube form a second nested combination, h) detecting the second nested combination of the second blood collection tube including the supported other said serum transfer cup by providing ultrasonic measurement information that identifies the first distinctively identifiable axial distance between the open end of the other said serum transfer cup and the flange top surface to identify the other said serum transfer cup while the other said serum transfer cup is supported on the second blood collection tube, and providing further ultrasonic measurement information that identifies the distance of the flange top surface from an ultrasonic signal transmitter when the other said serum transfer cup is supported on the second blood collection tube.

9. The method of claim 8 including providing information pertaining to liquid level in the nested one said serum transfer cup and the nested other said serum transfer cup by using ultrasonic signals that compare the liquid level in any of the nested serum transfer cups with the level of the open end of the respective said nested serum transfer cups.

10. A method of nesting a serum transfer cup on either of two different diameter blood collection tubes of the same axial height, but of different inside diameter and different outside diameter, wherein a first blood collection tube has an open end and a first inside diameter and a second blood collection tube has an open end and a second inside diameter of smaller magnitude than the first inside diameter comprising, a) forming a generally tubular serum transfer cup with a tubular wall having an open end, b) forming an external annular support flange of predetermined thickness on the tubular wall of the serum transfer cup stepped away from the open end of the serum transfer cup and with an outside flange diameter that is of greater magnitude than the outside diameter of the second blood collection tube and at least the same diameter as the outside diameter of the first blood collection tube, c) forming an enlarged annular collar portion on the tubular wall of the serum transfer cup, adjacent and below the annular support flange, with an outside collar diameter that is of lesser magnitude than the first inside diameter of the first blood collection tube to permit recession of the annular collar portion inside the first blood collection tube, and of greater magnitude than the inside diameter of the second blood collection tube to permit seating of a collar bottom surface of the enlarged collar portion on the second blood collection tube, d) forming a tubular section of the serum transfer cup below the enlarged collar portion with less outside diametrical magnitude than the first and second inside diameter of the first and second blood collection tubes to permit recession of the tubular section in the first and second blood collection tubes, e) supporting one said serum transfer cup on the first blood collection tube such that the external annular support flange is seated upon the open end of the first blood collection tube wherein the enlarged annular collar portion and the tubular section of the one said serum transfer cup are recessed in the first blood collection tube, and, f) supporting another said serum transfer cup on the second blood collection tube such that the collar bottom surface is seated upon the open end of the second blood collection tube, wherein the tubular section of the other said serum transfer cup is recessed in the second blood collection tube, while the flange top surface of the other serum transfer cup is elevated above the open end of the second blood collection tube, including providing the annular support flange with a flange top surface at a distinctively identifiable axial distance from the open end of the serum transfer cup and providing ultrasonic measurement information that identifies the distinctively identifiable axial distance between the open end of the serum transfer cup and the flange top surface to identify the presence of the serum transfer cup.

11. The method of claim 10 including measuring the distance of the support flange of the serum transfer cup from a fixed overhead location, when the serum transfer cup is supported in the first blood collection tube, to identify a nested combination of the serum transfer cup and the first blood collection tube.

12. The method of claim 10 including measuring the distance of the support flange of the serum transfer cup from a fixed overhead location, when the serum transfer cup is supported in the second blood collection tube, to identify the nested combination of the serum transfer cup and the second blood collection tube.

* * * * *

UNITED STATES PATENT AND TRADEMARK OFFICE
CERTIFICATE OF CORRECTION

PATENT NO. : 6,878,346 B2 Page 1 of 1
DATED : April 12, 2005
INVENTOR(S) : Thomas Deyoung, John Voulgaris and Loretta Vincent It is certified that error appears in the above-identified patent and that said Letters Patent is hereby corrected as shown below:

Column 8,
Line 6, after "than" insert -- the outside diameter of --

Column 10,
Line 42, change "the nested combination" to -- a nested combination --

Signed and Sealed this

Nineteenth Day of July, 2005

JON W. DUDAS
*Director of the United States Patent and Trademark Office*